United States Patent [19]
Kammerer

[11] Patent Number: 5,178,629
[45] Date of Patent: Jan. 12, 1993

[54] METHOD OF FORMING A SUTURE KNOT

[75] Inventor: Gene W. Kammerer, East Brunswick, N.J.

[73] Assignee: Ethicon, Inc., Somerville, N.J.

[21] Appl. No.: 845,292

[22] Filed: Mar. 3, 1992

[51] Int. Cl.⁵ .............................................. A61B 17/00
[52] U.S. Cl. ................................................... 606/224
[58] Field of Search ............................... 606/221–228; 289/1.2, 16; 112/222

[56] References Cited

U.S. PATENT DOCUMENTS

| | | | |
|---|---|---|---|
| 1,293,660 | 2/1919 | Armstrong | 606/225 |
| 2,715,486 | 8/1955 | Marcoff-Moghadam et al. | 606/224 |
| 3,762,418 | 10/1973 | Wasson | 606/226 |
| 4,182,341 | 1/1980 | Perri | 606/225 |
| 4,971,075 | 11/1990 | Lee | 606/224 |
| 5,074,874 | 12/1991 | Yoon et al. | 606/224 |
| 5,129,912 | 7/1992 | Noda et al. | 606/139 |

FOREIGN PATENT DOCUMENTS 0820811  4/1981  U.S.S.R. .............................. 606/224

OTHER PUBLICATIONS

Laparomed Corporation package insert, 1991, Suture Applier, Irvine, Calif.; Instrustruction brochure.

Primary Examiner—Stephen C. Pellegrino
Assistant Examiner—Gary Jackson
Attorney, Agent, or Firm—Matthew S. Goodwin

[57] ABSTRACT

A suture-needle combination is disclosed in which the suture has a plurality of adjacent loops, and a slip knot securing the first loop onto the free end of the suture. This suture configuration facilitates tying secure and stable knots endoscopically.

3 Claims, 3 Drawing Sheets

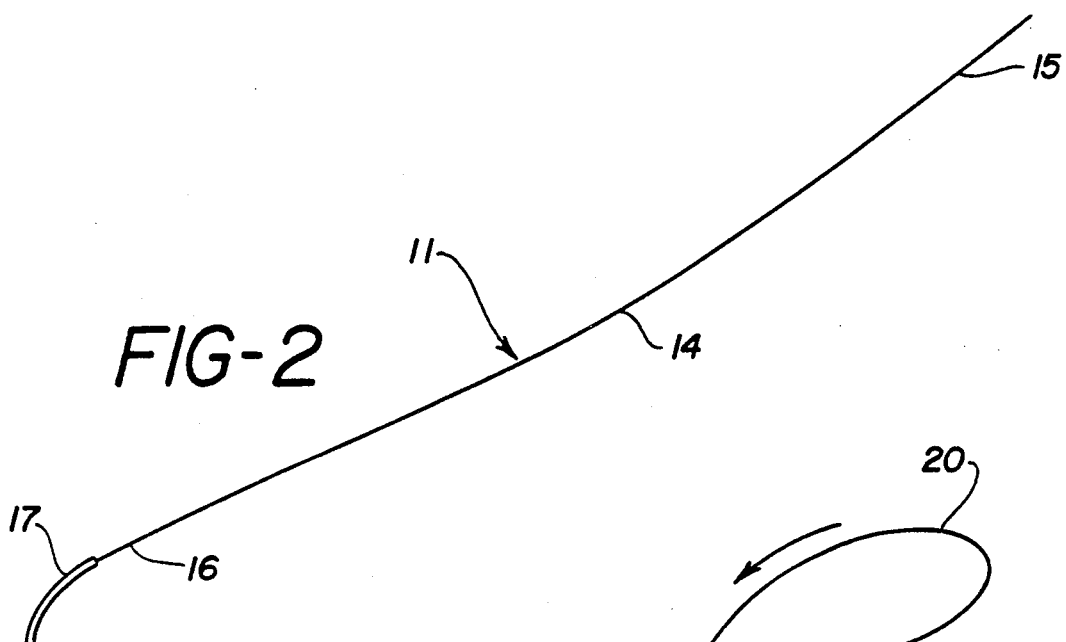
FIG-2
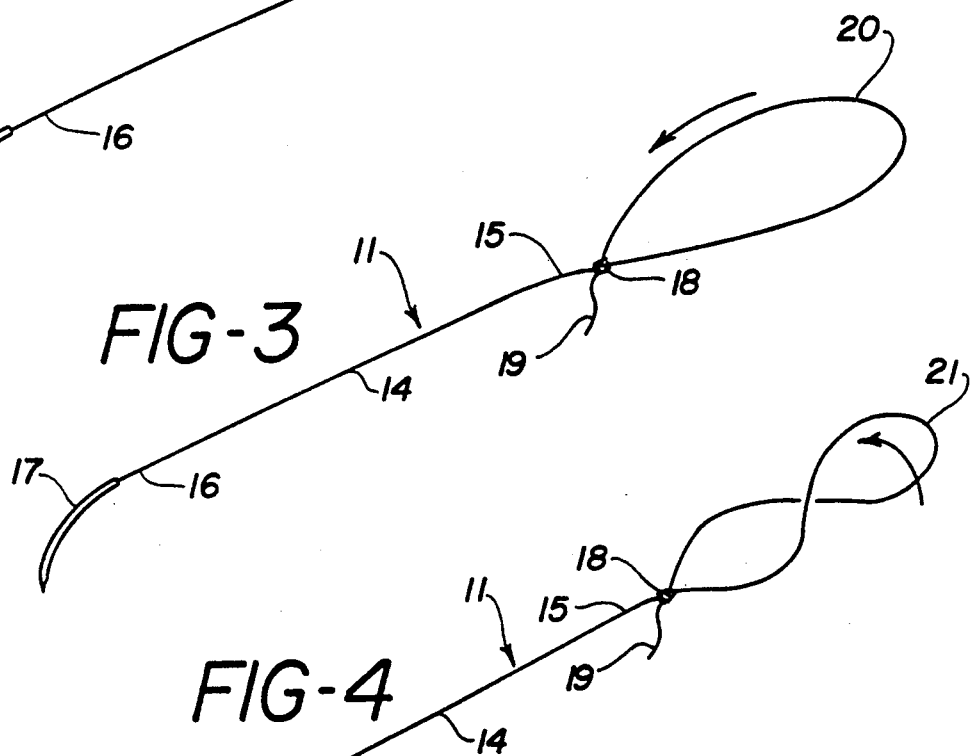
FIG-3
FIG-4
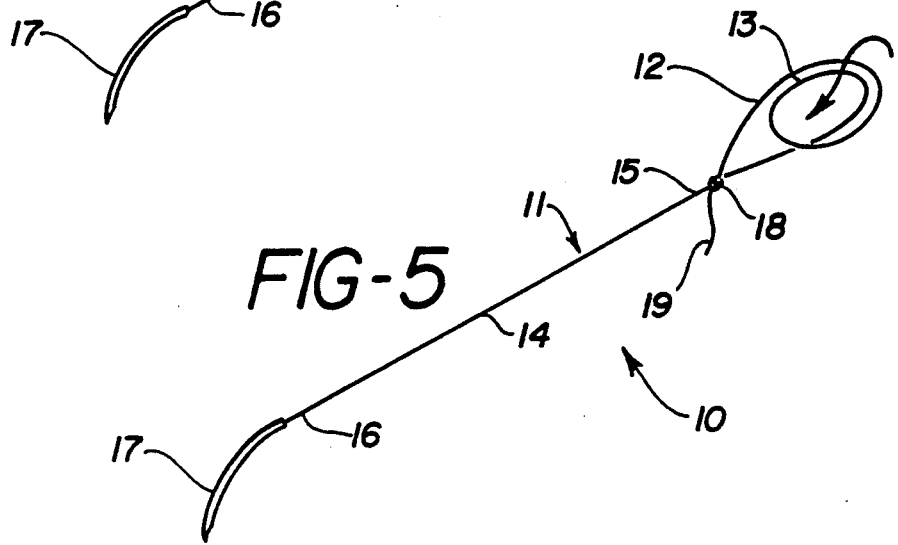
FIG-5

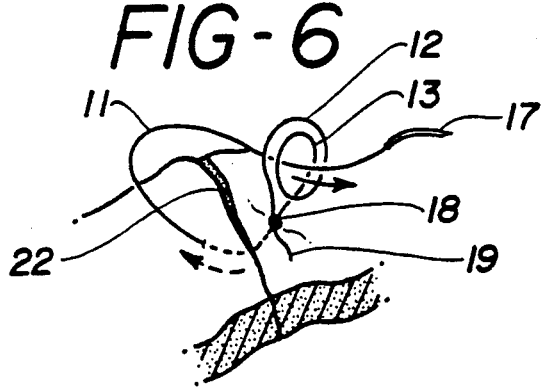
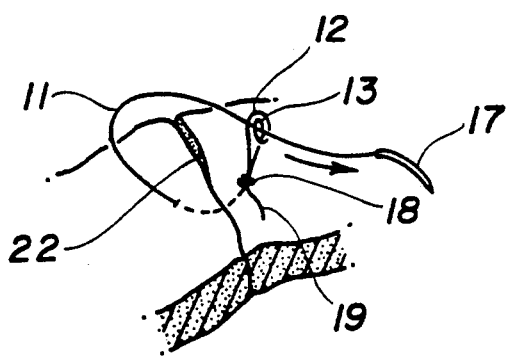
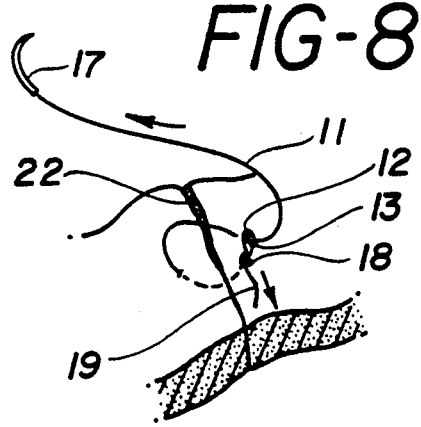
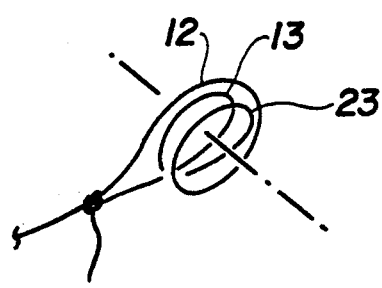
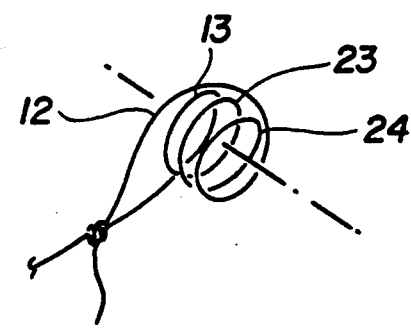

METHOD OF FORMING A SUTURE KNOT

BACKGROUND OF THE INVENTION

This invention relates to a suture-needle combination. More specifically, it relates to a novel suture configuation which facilitates tying a suture knot endoscopically.

As medical and hospital costs continue to increase, surgeons are constantly striving to develop advanced surgical techniques. Advances in the surgical field are often related to the development of operative techniques which involve less invasive surgical procedures and reduce overall patient trauma. In this manner, the length of hospital stays can be significantly reduced, and therefore the hospital and medical costs can be reduced as well.

One of the truly great advances in recent years to reduce the invasiveness of surgical procedures is endoscopic surgery. Endoscopic surgery involves the use of an endoscope, which is an instrument permitting the visual inspection and magnification of any cavity of the body. The endoscope is inserted through a cannula after puncture through the wall of the body cavity with a trocar, which is a sharp-pointed instrument. The surgeon can then perform diagnostic and therapeutic procedures at the surgical site with the aid of specialized instrumentation designed to fit through additional cannulas providing openings into the desired body cavity as may be required.

In the vast majority of surgical procedures, including those involved in endoscopic surgery, it is necessary to close wounds with sutures. The integrity of the suture closing depends on not only the type of suture used, but also the knot configuration used for tying suture strands.

Surgeons and physicians commonly rely on two types of knots when working with sutures: a) a stay suture knot, and b) an interrupted stitch knot. The stay suture knot, often referred to as an "anchor" knot, is used by the surgeon to anchor a suture in tissue for a continuous line of stitches. The anchor enables the surgeon to stitch a continuous line of stitches and yet maintain the integrity of the closure with the anchor knot. Since the continuous line of stitches provides a significant amount of security for closure, the degree of strength required for the stay suture knot is not as great as that for an interrupted stitch knot.

An interrupted stitch knot is truly an independent knot. It is frequently used during tissue repair to improve the security of closure of a wound. The interrupted stitch knot may be used at the conclusion of closure of an incision after a continuous line of stitches has been laid by the surgeon. Once the continuous line of stitches is laid, the surgeon will tie an interrupted stitch knot to provide the greatest amount of security which he is capable of providing. The interrupted stitch knot is a knot used for tying two ends of a single suture strand together in one stitch. It does not rely on a cumulative row of stitches for additional strength, so it is critical that an interrupted stitch knot have a high degree of security and strength.

Unfortunately, the required degree of security of suture knots is difficult to achieve during endoscopic operations because of the difficulty of maneuvering a suture strand within such closed quarters. This is especially true in those situations where it is necessary or desirable for the surgeon to tie an interrupted stitch knot, which requires the greatest amount of security and strength. The tying of such knots frequently is time consuming and laborious even under optimum conditions, and is especially so during endoscopic conditions. In view of these difficulties, it would be most desirable if a new suture configuration could be fabricated which would allow the surgeon or physician to easily tie a suture knot with the requisite amount of strength and security in a short time period.

SUMMARY OF THE INVENTION

The invention is a suture-needle combination. It comprises a suture having a first loop, a second loop adjacent to the first loop, and a free end having a proximal section and a distal section. The suture also has a slip know with a knot pulling end, and the slip knot secures the first loop onto the proximal section of the free end of the suture. A needle is attached to the distal section of the free end of the suture.

The suture-needle combination of this invention is particularly adapted for use during endoscopic surgical techniques, although it can also be used during any conventional surgical procedure. Once the needle and suture are passed through desired bodily tissue, it is relatively easy to secure a tight knot against the bodily tissue, even endoscopically. Surprisingly, such a knot has a degree of strength and security equal or superior to conventional suture knots, such as the stay suture knot and the interrupted stitch knot. The suture-needle combination can be used during any operative procedure requiring the suturing of bodily tissue.

BRIEF DESCRIPTION OF THE DRAWINGS

FIGS. 2-5 show the sequence of steps necessary to configure a conventional suture-needle combination into the suture-needle combination of this invention.

FIGS. 6-8 show the sequence of steps necessary to tighten a slip knot of the suture-needle combination for suturing an incisional wound.

FIGS. 9 and 10 are partial perspective views of alternative embodiments of the suture-needle combination of this invention.

DESCRIPTION OF THE PREFERRED EMBODIMENT

Figure 1:
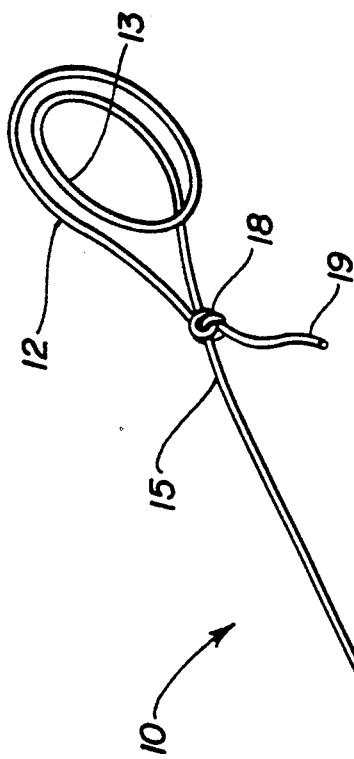
FIG. 1 is a perspective view of the suture-needle combination of this invention.

Referring to FIG. 1, there is shown a suture needle combination 10. It has a suture 11 with a first loop 12 and a second loop 13 adjacent to the first loop. The suture has a free end 14 with proximal section 15 and distal section 16. As used herein, "distal" is used to describe that portion of the suture-needle combination which extends away from the user during use, and "proximal" is used to describe that portion of the combination that extends toward the user during use.

Attached to the suture is surgical needle 17. The needle is attached at distal section 16 of the free end of the suture. Attachment of the needle to the suture can be accomplished using any of the conventional swaging techniques, or by any other method which can be envisioned for such attachment.

First loop 12 of the suture is secured to proximal section 15 of the free end of the suture with slip knot 18. The slip knot terminates with knot pulling end 19. The slip knot can be any knot configuration which will allow the suture to slide through the knot in one direction but prevent sliding movement in the opposite direction. In this embodiment, the slip knot allows the suture to slide in the direction which will result in a tightening of the loops. In addition, the knot must be of such a size that its diameter is larger than the diameter made form the penetration of the needle-suture combination through bodily tissue.

The suture can be composed of any suitable material which can be processed to prepare a filamentary strand. For example, the suture can be composed of an absorbable or nonabsorbable material, and it can be configured as a braid, or if desired, as a monofilament. The preferred nonabsorbable material is polyester. The preferred absorbable materials are derived from homopolymers and copolymers of glycolide, lactide, ε-caprolactone, p-dioxanone, and trimethylene carbonate. The suture-needle combination of this invention can be easily configured from a conventional suture strand attached to a needle. As shown in FIGS. 2-5, suture strand 11 is first manipulated in the manner shown in FIG. 3 to prepare a precursor loop 20 with the requisite slip knot 18 and knot pulling end 19. Precursor loop 20 is twisted to form a figure eight loop 21 as shown in FIG. 4. The top half of the figure eight loop is then manipulated as shown in FIG. 5 to prepare the first loop 12 and adjacent second loop 13 of the suture-needle combination of the invention. Preferably, the second adjacent loop is in substantial coaxial alignment with the first loop to facilitate the successful operation of the suture needle combination.

In use, the suture-needle combination is first placed within convenient proximity to bodily tissue which is desired to be sutured. If an endoscopic procedure is being performed, then the suture-needle combination can be placed at the area of such bodily tissue by transferring the combination into the body through a small opening made by a trocar. This transfer can be easily facilitated with the use of suitable endoscopic instruments.

Figure 1A:
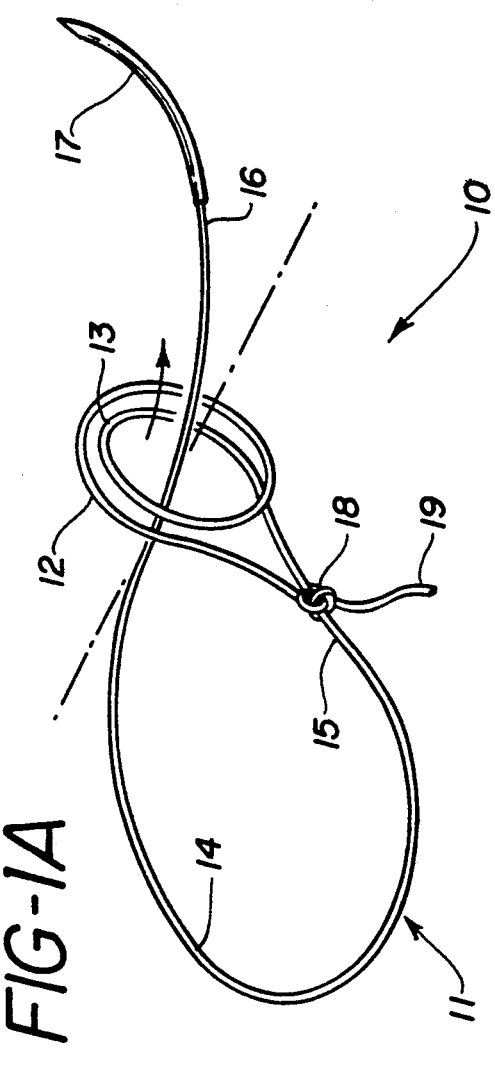
FIG. 1A is a perspective view of the suture-needle combinations of FIG. 1 in its configuration during use.

Once the suture-needle combination is placed at the appropriate surgical site, the use of the suture-needle combination for tying a secure knot can be visualized as shown in FIGS. 6-8. Using an appropriate surgical instrument, the user grasps the needle and penetrates bodily tissue with the needle at or near the incisional wound 22 which is desired to be sutured, and then passes the needle through the tissue until it penetrates the other side of the incisional wound. Once the needle is passed through both sides of the incisional site, it is pulled away from the tissue until the slip knot contacts the tissue at the point of entry of the needle. At this point, the needle is passed through each of the loops. The configuration of the suture-needle combination when the needle is passed through the loops can best be seen at FIG. 1A. To continue the operation, the user continues to pull the needle in a direction away from the loops. As shown in FIG. 7, the free end of the suture attached to the needle passes through the loops, and the diameter of the loops accordingly decreases until the loops subsequently tighten about the suture. Once the loops are tightened about the suture, the knot so formed is "locked" as shown in FIG. 8 by simultaneously pulling the needle and the knot pulling end of the slip knot in opposite directions. This locking action increases knot strength.

To further increase the knot strength, additional loops can easily be configured. As illustrated in FIGS. 9 and 10, a third loop 23, as well as a fourth loop 24, can be added to the suture-needle combination if so desired. Preferably, each of the additional loops are adjacent to, and in substantial coaxial alignment with, the first and second loops.

EXAMPLES

Test Method

The strength of a suture knot is tested in a tensile testing device (Instron 4201). The strength of the knot is measured by its resistance to opening due to forces applied from inside the loop. A special fixture was fabricated to properly secure, then test the knot strength. The standard jaws of the instron were equipped with the fixture which consists of two plates, one on each jaw, lower and upper. Each plate is 1¼ in. wide by 2½ in. long. These are placed vertically in the jaws. On the inner ends of each plate a semi-circle pin is attached on a 90° axis to the face of the plate. When the jaws are closed and the pins come together they form a cylinder. The bottom pin has a rubber tube, 1/16 in. wall thickness, placed over it. The plate with the bottom pin also has a small block attached which has a notch that surrounds the pin. The block thickness is ½ the length of the pin. The notch allows the suture to slide around the pin, but the distance between the block and the pin at the notch is such that the knot can not slide through. This provides the resistance for cinching the knot.

The method for preparing and testing the knot is as follows:

1. A suture meeting the configuration required for the suture-needle combination of this invention is tied and the knot is placed in the notch on the lower stationary jaw. The free end of the suture is wrapped around the pin on the upper movable jaw and threaded through the loop. The jaws are in the fully closed position.

2. The knot is placed at the front of the notch just touching the pin.

3. By pulling on the free end of the suture, the loops are contracted until they are secure around this tail. The tension to cinch the knot can be between 1 lb. and 4 lbs., but is standardized at 3 lbs.

4. Once the loops have cinched completely around the free end, tension is applied to the knot pulling end of the suture. This force should equal the cinching force.

5. The jaws are then separated by raising the upper jaw at a rate of 1 in./min.

6. As the jaws separate the resistance of the knot to opening is monitored and recorded in lbs.

7. The jaws are separated to a distance of ½ in. and the peak force recorded is the knot strength.

| Comparison of Loops from a Nonabsorbable Braid (U.S.P. Size 2/0) Maximum Tensile in Lbs. | | | |
| --- | --- | --- | --- |
| 1 Loop | 2 Loops | 3 Loops | 4 Loops |
| 0.66 | 6.71 | 8.31 | 5.85 |
| 2.11 | 5.52 | 6.14 | 6.85 |
| 2.40 | 5.92 | 5.83 | 5.54 |
| 0.34 | 1.58 | 7.15 | 3.93 |
| 1.53 | 2.76 | 4.91 | 4.92 |
| 0.61 | 2.86 | 5.01 | 6.72 |
| 0.52 | 4.98 | 7.31 | 5.07 |
| 1.04 | 2.99 | 4.68 | 2.98 |
| 1.82 | 2.84 | 6.23 | 5.767 |
| 1.18 | 3.15 | 5.57 | 3.02 |

Comparison of Loops from a Nonabsorbable Braid (U.S.P. Size 2/0)

Maximum Tensile in Lbs

|  | 1 Loop | 2 Loops | 3 Loops | 4 Loops |
|---|---|---|---|---|
| mean | 1.17 | 3.91 | 6.11 | 5.06 |

Conclusion: A higher number of loops provided for greater knot strength. It was observed that as the number of loops increased the consistency of the knot was more difficult to achieve. The mass of the loops begins to interfere with its tightening. That appears to be evident in the plateau of the strength between 3 and 4 loops.

Comparison of Different Suture Types

| | Monofilament (U.S.P. Size 2/0) 3 Loops | Absorbable Braid (U.S.P. Size 2/0) 2 Loops |
|---|---|---|
| | 3.15 | 3.66 |
| | 2.35 | 3.46 |
| | 2.63 | 2.90 |
| | 1.88 | 3.31 |
| | 2.47 | 3.98 |
| mean | 2.50 | 3.87 |
| | | mean 3.53 |

Conclusion: The monofilament is more difficult to hold than the braid. However, multiple loops provide high knot strengths. Due to the smoothness of the monofilament and its resistance to bending it did not match the braid in knot strength for similarly constructed loop knots.

Comparison of Different Knots

All samples are 2 loops on braided suture (U.S.P. Size 2/0)

| Single Throw with ½ Hitch | Conventional "Roeder" Knot | Roeder w/ ½ Hitch in Loops |
|---|---|---|
| 2.17 | 4.75 | 3.18 |
| 4.43 | 2.12 | 3.24 |
| 5.11 | 4.07 | 3.05 |
| 2.36 | 4.06 | 3.14 |
| 5.75 | 2.80 | 3.49 |
| mean 3.96 | 3.56 | 3.22 |

Conclusion: The specific configuration of the knot does not appear to have a significant bearing on the final strength. The number of loops are more important.

While this invention has been described in its preferred embodiment, numerous additional embodiments and modes of operation can well be envisioned by those skilled in this particular art. This description should not be construed in any way to limit the scope of the claimed invention.

I claim:

1. A method of forming a suture unit, comprising the steps of:
   a) providing a suture having a precursor loop, a free end having a proximal section and a distal section, a slip knot with a knot pulling end, said slip knot securing said precursor loop onto said proximal section of said free end, and a needle attached to said distal section of said free end;
   b) twisting said precursor loop so as to form a figure eight loop; and
   c) manipulating said figure eight loop in a manner so as to provide a first loop and an adjacent second loop in substantial coaxial alignment with said first loop ; and (d) passing said needle through bodily tissue, which is desired to be sutured; and (e) passing the needle through first loop and the adjacent second loop, and pulling the needle in a direction away from said first and second adjacent loop until said first and said second adjacent loops subsequently tightening about said suture, thereby forming a knot.

2. The method of claim 1, wherein said precursor loop is twisted so as to form a third loop, and manipulating said third loop in a manner so as to provide said third loop adjacent to, and in substantial coaxial alignment with, said first and second loops.

3. The method of claim 1, wherein said precursor loop is twist so as to form a forth loop, and manipulating sad forth loop in a manner so as to provide said fourth loop a adjacent to, and in substantial coaxial alignment with, said first, second and third loops.

* * * * *